United States Patent
Lane et al.

(10) Patent No.: US 8,268,763 B2
(45) Date of Patent: Sep. 18, 2012

(54) ENZYMATIC DEGRADATION OF COLORANT IN LENS CARE SOLUTIONS

(75) Inventors: Jennifer Dawn Lane, Stone Mountain, GA (US); Mary Mowrey-McKee, Alpharetta, GA (US); Karen Belinda Sentell, Alpharetta, GA (US); Karen Frances Lindley, Cumming, GA (US)

(73) Assignee: Novartis AG, Basel (CH)

( * ) Notice: Subject to any disclaimer, the term of this patent is extended or adjusted under 35 U.S.C. 154(b) by 217 days.

(21) Appl. No.: 12/310,189

(22) PCT Filed: Aug. 14, 2007

(86) PCT No.: PCT/US2007/017961
§ 371 (c)(1),
(2), (4) Date: Feb. 12, 2009

(87) PCT Pub. No.: WO2008/021348
PCT Pub. Date: Feb. 21, 2008

(65) Prior Publication Data
US 2009/0247443 A1 Oct. 1, 2009

Related U.S. Application Data

(60) Provisional application No. 60/838,114, filed on Aug. 16, 2006.

(51) Int. Cl.
*C11D 3/386* (2006.01)
(52) U.S. Cl. .................................................. 510/114
(58) Field of Classification Search .................. 510/114
See application file for complete search history.

(56) References Cited

U.S. PATENT DOCUMENTS

| 4,826,658 | A  | * | 5/1989  | Kay .................................. 422/30 |
| 5,578,240 | A  | * | 11/1996 | Park et al. ...................... 510/513 |
| 5,605,667 | A  | * | 2/1997  | Powell, Jr. ..................... 422/119 |
| 5,630,884 | A  |   | 5/1997  | Huth ............................... 134/27 |
| 6,099,800 | A  |   | 8/2000  | Cheng ............................ 422/30 |
| 6,210,639 | B1 |   | 4/2001  | Vlass et al. ..................... 422/29 |
| 6,440,411 | B2 |   | 8/2002  | Scherer et al. ................ 424/94.4 |
| 2001/0033843 | A1 | * | 10/2001 | Scherer et al. ........... 424/195.17 |
| 2002/0069896 | A1 | * | 6/2002  | Pankow ............................. 134/6 |

FOREIGN PATENT DOCUMENTS

| WO | WO 94/18297 |   | 8/1994  |
| WO | WO 95/30021 | * | 11/1995 |

OTHER PUBLICATIONS

PCT International Search Report, Dec. 2007.
PCT Written Opinion of the International Searching Authority, Dec. 2007.

* cited by examiner

*Primary Examiner* — John Hardee
(74) *Attorney, Agent, or Firm* — Sheng-Hsin Hu; Jian Zhou

(57) ABSTRACT

The present invention provides a lens care kit for disinfecting and cleaning contact lenses. The lens care kit of the invention comprises a colored lens care solution including a colored protein and a proteolytic enzyme. The kit of the invention allows customers to visually identify when their lenses are disinfected, clean, and ready to wear. The invention relies upon a color change to indicate the completion of disinfection and cleaning of contact lenses.

16 Claims, No Drawings

ENZYMATIC DEGRADATION OF COLORANT IN LENS CARE SOLUTIONS

This application is a national stage filing under 35 U.S.C. 371 of International Application No. PCT/US2007/017961 filed Aug. 14, 2007, which claims benefits of United States provisional application number 60/838,114 filed Aug. 16, 2006.

This invention relates generally to use of selective degradation of a colorant in a lens care solution as a color indicator for cleaning and disinfecting a contact lens. In particular, the invention provides a system, methods, and kits useful for cleaning and disinfecting contact lenses.

BACKGROUND OF THE INVENTION

Contact lenses provide a means for vision correction for a wide range of consumers. The advantages of contact lens wear are numerous. Improved convenience and improved appearance in comparison to spectacle glasses are probably the two most important advantages to most consumers. However, contact lenses require stringent care regimes in order to ensure comfort and avoid ocular infections. Proper care of contact lenses typically requires the consumer to periodically clean and disinfect the lenses, to prevent infection or other deleterious effects on ocular health which may be associated with contact lens wear.

In recent years, multiple-purpose solutions, which clean, disinfect, and rinse contact lenses all without mechanically rubbing lenses, have been developed as a new type of lens care systems. These new systems are dominating most of the lens care market. Such popularity is most likely derived from the ease and convenience provided by these new systems to consumers. In order to achieve satisfactory disinfection, a contact lens has to be in a MPS solution for a sufficient time period. However, customers currently do not have a direct way to determine if their lenses have been in the lens care solution long enough to ensure that the lenses are sufficiently disinfected. It would be desirable to provide customers with a means by which they could visually identify when their lenses are clean and ready to wear.

Therefore, there exists a need for a lens care kit capable of decolorizing over the time period required for disinfection of contact lenses, in order to provide the consumer with a visual indication that the lens care regimen is complete.

SUMMARY OF THE INVENTION

The present invention provides a lens care kit for cleaning and disinfecting contact lenses, comprising a colored lens care solution including at least one water-soluble colored protein and a proteolytic enzyme, wherein, when in contact with the colored lens care solution, the proteolytic enzyme gradually degrades the colored protein over a time period sufficient to substantially decolorize the colored lens care solution, thereby indicating that lenses being disinfected and cleaned by the colored lens care solution are ready for use. The lens care kit of the invention allows customers to visually identify when their lenses are disinfected, clean, and ready to wear.

The present invention provides the foregoing and other features, and the advantages of the invention will become further apparent from the following detailed description of the example embodiments set forth herein. The detailed description is merely illustrative of the invention and do not limit the scope of the invention, which is defined by the appended claims and equivalents thereof.

DETAILED DESCRIPTION OF PREFERRED EMBODIMENTS

The present invention may be understood more readily by reference to the following detailed description of the invention, which form a part of this disclosure. Unless defined otherwise, all technical and scientific terms used herein have the same meaning as commonly understood by one of ordinary skill in the art to which this invention belongs. Generally, the nomenclature used herein is well known and commonly employed in the art. Conventional methods are used for carrying out the disclosed procedures, such as those provided in the art and various general references. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, reference to singular forms such as "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The invention, in one aspect, provides a lens care kit for cleaning and disinfecting contact lenses, comprising a colored lens care solution including at least one water-soluble colored protein and a proteolytic enzyme, wherein, when in contact with the colored lens care solution, the proteolytic enzyme gradually degrades the colored protein over a time period sufficient to substantially discolor the colored lens care solution, thereby indicating that lenses being disinfected and cleaned by the colored lens care solution are ready for use.

A lens care kit of the invention can be used to disinfect and clean contact lenses including hard (PMMA) contact lenses, soft (hydrophilic) contact lenses, and rigid gas permeable (RGP) contact lenses. The soft contact lenses are hydrogel contact lenses or silicone hydrogel contact lenses.

A "hydrogel" refers to a polymeric material which can absorb at least 10 percent by weight of water when it is fully hydrated. Generally, a hydrogel material is obtained by polymerization or copolymerization of at least one hydrophilic monomer in the presence or absence of additional monomers and/or macromers.

A "silicone hydrogel" refers to a hydrogel obtained by copolymerization of a polymerizable composition comprising at least one silicone-containing vinylic monomer or at least one silicone-containing macromer.

"Hydrophilic," as used herein, describes a material or portion thereof that will more readily associate with water than with lipids.

The lens care kit of the invention allows customers to visually identify when their lenses are disinfected, clean, and ready to wear. The invention relies upon the disappearance or fading of color to indicate when disinfection and cleaning of contact lenses is complete. Preferably, the initial color is blue or green or purple. It is understood that any other color can be used.

In accordance with the invention, the lens care solution has a color that gradually fades over a controlled time period. Preferably, at the end of the controlled time period, the color of the lens care solution disappears substantially and becomes substantially clear (substantially colorless but transparent). The controlled time period is sufficiently long for disinfecting contact lenses and is preferably at least about 2 hour, more preferably about 4 hours, even more preferably about 6 hours.

A colored lens care solution of the invention comprises at least one water-soluble colored protein. In accordance with the invention, the colored protein can be any naturally colored proteins so long as they are not toxic and does not foul or stain contact lenses and lens cases. Examples of colored proteins include, without limitation, phycobiliproteins, green fluorescent proteins (GFPs), GFP-like proteins, bacteriorhodopsin, blue-copper protein (e.g., plastocyanin) and the likes. Exemplary phycobiliproteins include without limitation phycocyanine, allophycocyanine, and phycoerythrin.

Preferred colored proteins are phycocyanine and allophycocyanine. These colored proteins can be harvested as the extract of an alga from naturally grown plants and are useful for providing an intense and long-lasting tint to lens care solutions. When contact lenses are treated with such a solution, they are not tinted by the algal extract in a manner visible to the naked eye. This is due, inter alia, to the typically high molecular weight of the algal extracts, which molecular weight is well above 200,000 in the case of the *Spirulina platensis* extract.

The algal extract is preferably blue or green, more preferred blue. A preferred class of alga the extract of which is useful in the present invention is blue alga (*Spirulina* type), more preferred is the Japanese blue alga (*Spirulina platensis*). Other known. *Spirulina* species are *Spirulina gigantea* or *Spirulina maxima*. Typical extracts which are useful as protein colorants in the context of this invention are LinaBlue AE (a partially purified form of allophycocyanin) from *Spirulina* algae, LinaBlue HGE, LinaBlue A (about 30% Phycocyanin), LinaBiue HK (about 60% Phycocyanin) and Lineablue HG (about 70% Phycocyanin), all of which are marketed by Dainippon Ink & Chemicals Inc., Japan. Another suitable product is *Spirulina* blue distributed by Tokai Sangyo Co. Ltd, Japan. Purified allophycocyanin and phycocyanin are available from Sigma.

In accordance with the invention, one or more colorants can be used together in the colored lens care solution to create the desired color. A person skilled in the art will know how to select types of colorants and amounts thereof to achieve a desired color.

In accordance with the invention, a colored lens care solution is ophthamically safe. The term "ophthalmically safe" with respect to a lens care solution is meant that a contact lens treated with the solution is safe for direct placement on the eye without rinsing, that is, the solution is safe and sufficiently comfortable for daily contact with the eye via a contact lens. An ophthalmically safe solution has a tonicity and pH that is compatible with the eye and comprises materials, and amounts thereof, that are non-cytotoxic according to international ISO standards and U.S. FDA regulations:

The term "compatible with the eye" means a solution that may be in intimate contact with the eye for an extended period of time without significantly damaging the eye and without significant user discomfort.

A colored lens care solution can be a prepared from any lens care solution including commercially available lens care solutions by adding one or more colorants therein. A lens care solution can be a multiple purpose solution (free of hydrogen peroxide) or a hydrogen peroxide-containing solution.

Where a lens care solution is a hydrogen peroxide-containing solution, the colored lens care solution is preferably prepared immediately prior to lens disinfection in a lens case by mixing two solutions, one hydrogen peroxide-containing solution free of colorant and the other solution containing colorant and free of hydrogen peroxide. Such mixing can be achieved used a container having two separate compartments, one for the hydrogen peroxide-containing solution and the other for the colorant-containing solution free of hydrogen peroxide. The container can further comprise a mixing mechanism known to a person skilled in the art to mix the two solutions when pouring out the two solutions from the container. By separately storing a hydrogen peroxide-containing solution and a colorant-containing solution and mixing them on-demand to form a colored lens care (disinfecting) solution, one may minimize or eliminate the possibility of the colorant being oxidized slowly by hydrogen peroxide and thereby greatly increases the shelf life of the solutions.

In accordance with the invention, a hydrogen peroxide containing solution can further comprise other components known to a person skilled in the art, for example, tonicity agent (e.g., sodium chloride, potassium chloride, mannitol, xylitol, dexpenthanol, dextrose, glycerin, propylene glycol, and mixture thereof), conditioning/wetting agents (polyvinyl alcohol, polyoxamers, polyvinyl pyrrolidone, hydroxypropyl cellulose, and mixtures thereof), buffering agents, surfactants, and the like.

Where a lens care solution is a hydrogen peroxide-free disinfecting solution, such as, for example, a multiple purpose solution, a colorant can be directly added to it to prepare a colored lens care solution of the invention, because of the absence of hydrogen peroxide.

In a preferred embodiment, the lens care solution of the invention is a multipurpose solution capable of disinfecting, cleaning, and rinsing a contact lens.

The term "disinfecting solution" means a solution containing one or more microbicidal compounds, that is effective for reducing or substantially eliminating the presence of an array of microorganisms present on a contact lens, which can be tested by challenging a solution or a contact lens after immersion in the solution with specified inocula of such microorganisms.

A solution that is useful for cleaning, chemical disinfection, storing, and rinsing an article, such as a contact lens, is referred to herein as a "multi-purpose solution." Such solutions may be part of a "multi-purpose solution system" or "multi-purpose solution package." The procedure for using a multi-purpose solution, system or package is referred to as a "multi-functional disinfection regimen." Multi-purpose solutions do not exclude the possibility that some wearers, for example, wearers particularly sensitive to chemical disinfectants or other chemical agents, may prefer to rinse or wet a contact lens with a another solution, for example, a sterile saline solution prior to insertion of the lens. The term "multi-purpose solution" also does not exclude the possibility of periodic cleaners not used on a daily basis or supplemental cleaners for removing proteins, for example enzyme cleaners, which are typically used on a weekly basis.

A colored hydrogen peroxide-free disinfecting solution of the invention can be used to disinfect contact lenses against a wide range of microorganisms including but not limited to *Fusarium solani, Staphylococcus aureus, Pseudomonas aeruginosa, Senatia marcescens* and *Candida albicans*. For the purposes of the present invention the term "disinfect"

means the rendering non-viable of substantially all pathogenic microbes that are in the vegetative state, including gram negative and gram positive bacteria, as well as fungi. The chemical compounds and compositions that render such pathogenic microbes inactive are known as microbicides.

A colored disinfecting or MPS solution of the invention must contain a microbicide in a concentration sufficient to effect the desired disinfection of a contact lens. The specific concentrations required for the microbicides useful in this invention must be determined empirically for each microbicide. Some of the factors affecting the effective concentration are specific activity of the microbicide against the specified pathogens, the molecular weight of the microbicide, and the solubility of the microbicide. It is also important that the chosen microbicides be employed in a physiologically tolerable concentration. The list of microbicides which may be employed in the present invention include, but is not limited to biguanides, biguanide polymers, salts thereof, N-alkyl-2-pyrrolidone, polyquaternium-1, bronopol, benzalkonium chloride, and hydrogen peroxide. The presently-useful antimicrobial biguanides include biguanides, biguanide polymers, salts thereof, and mixtures thereof. Preferably, the biguanide is selected from alexidine freebase, salts of alexidine, chlorhexidine freebase, salts of chlorhexidine, hexetidine, hexamethylene biguanides, and their polymers, and salts thereof. Most preferably, the biguanide is a hexamethylene biguanide polymer (PHMB), also referred to as polyaminopropyl biguanide (PAPB).

Typical solutions of this invention contain the microbicides PHMB in an amount of from about 0.01 to about 10 ppm, preferably from about 0.05 to about 5 ppm, more preferably from about 0.1 to about 2 ppm, even more preferably from about 0.2 to about 1.5 ppm.

The present solutions preferably include an effective amount of a chelating component. Any suitable, preferably ophthalmically acceptable, chelating component may be included in the present compositions, although ethylenediaminetetraacetic acid (EDTA), salts thereof and mixtures thereof are particularly effective. EDTA is a low level practically non-irritating chelating agent and can be synergistic with PHMB to increase antimicrobial efficacy. The typical amount of EDTA is from about 0.001% to about 1% by weight, preferably from about 0.002% to about 0.5% by weight, more preferably from about 0.004% to about 0.1, even more preferably from about 0.005% to about 0.05, based on the total amount of contact lens care composition.

The solution of the present invention preferably contains a buffering agent. The buffering agents maintain the pH preferably in the desired range, for example, in a physiologically acceptable range of about 6.0 to about 8.0. Any known, physiologically compatible buffering agents can be used. Suitable buffering agents as a constituent of the contact lens care composition according to the invention are known to the person skilled in the art. Examples are boric acid, borates, e.g. sodium borate, citric acid, citrates, e.g. potassium citrate, bicarbonates, e.g. sodium bicarbonate, TRIS (trometamol, 2-amino-2-hydroxymethyl-1,3-propanediol), bis-aminopolyols, phosphate buffers, e.g. $Na_2HPO_4$, $NaH_2PO_4$, and $KH_2PO_4$ or mixtures thereof. The amount of each buffer agent is that amount necessary to be effective in achieving a pH of the composition of from about 6.5 to about 7.5. Typically, it is present in an amount of from 0.001% to 2%, preferably from 0.01% to 1%; most preferably from about 0.05% to about 0.30% by weight.

The preferred buffering agents are bis-aminopolyols of formula (I)

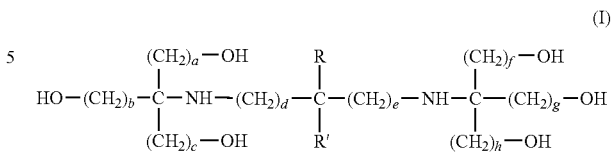

wherein a, b, c, d, e, f, g, and h are independently an integer from 1 to 6; and R and R' are independently selected from the group consisting of —H, —$CH_3$, —$(CH_2)_{2-6}$—H, and —$(CH_2)_{1-6}$—OH. In the present invention, the buffering agents described by formula (I) may be provided in the form of various water-soluble salts. A most preferred bis-aminopolyol is 1,3-bis(tris[hydroxymethyl]methylamino)propane (bis-TRIS-propane).

It has been found that bis-TRIS-propane can exhibit a synergy with certain microbicides (e.g., PHMB) and fungicides, resulting in a microcidal activity significantly higher than the activity of these same active ingredients used in conjunction with other buffers. BIS-TRIS propane is described under biological buffers in Biochemicals and Reagents, Sigma-Aldrich Co., 2000-2001 edition. The specific structure of bis-TRIS-propane is shown in formula II.

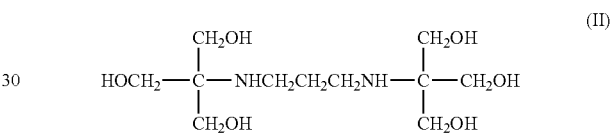

The dissociation constants for this dibasic compound are $pKa_1=6.8$ and $pKa_2=9.5$ which renders aqueous solutions of this compound useful as a buffering agent in a broad pH range from about 6.3 to 9.3. Bis-TRIS-propane at concentrations used in this invention is harmless to the eye and to known contact lens materials and is, therefore, ophthalmically compatible.

A colored lens care solution of the invention preferably comprises a lubricant. "Lubricants" as used herein refer to any compounds or materials which can enhance surface wettability of a contact lens and/or the eye or reduce the frictional character of the contact lens surface. Examples of lubricants include without limitation mucin-like materials and hydrophilic polymers.

Exemplary mucin-like materials include without limitation polyglycolic acid, polylactides, collagen, and gelatin. A mucin-like material may be used to alleviate dry eye syndrome. The mucin-like material preferably is present in effective amounts.

Exemplary hydrophilic polymers include, but are not limited to, polyvinylalcohols (PVAs), polyamides, polyimides, polylactone, a homopolymer of a vinyl lactam, a copolymer of at least one vinyl lactam in the presence or in the absence of one or more hydrophilic vinylic comonomers, a homopolymer of acrylamide or methaacrylamide, a copolymer of acrylamide or methacrylamide with one or more hydrophilic vinylic monomers, mixtures thereof.

The solution may also contain one or more viscosity-enhancing agents. Suitable viscosity-enhancing components include, but are not limited to, polyvinylpyrrolidone, water soluble natural gums, cellulose-derived polymers, and the like. Useful natural gums include guar gum, gum tragacanth and the like. Examples of useful cellulose-derived polymers as viscosity-enhancing agents include without limitation cellulose ethers.

Exemplary preferred cellulose ethers are methyl cellulose (MC), ethyl cellulose, hydroxymethylcellulose, hydroxyethyl cellulose (HEC), hydroxypropylcellulose, hydroxypropylmethyl cellulose (HPMC), or a mixture thereof. More preferably, a cellulose ether is hydroxyethyl cellulose (HEC), hydroxypropylmethyl cellulose (HPMC), and mixtures thereof. The cellulose ether is present in the composition in an amount of from about 0.01% to about 5% by weight, preferably from about 0.05% to about 3% by weight, even more preferably from about 0.1% to about 1% by weight, based on the total amount of contact lens care composition. It is believed that a cellulose ether can be used to increase the viscosity of a lens care product and also can serve as a lubricant in the lens care composition.

A useful viscosity-enhancing component is polyvinylpyrrolidone (PVP). The polyvinylpyrrolidone (PVP) used in the compositions of the invention is a linear homopolymer or essentially a linear homopolymer comprising at least 90% repeat units derived from 1-vinyl-2-pyrrolidone monomers, the polymer more preferably comprising at least about 95% or essentially all of such repeat units, the remainder selected from polymerization-compatible monomers, preferably neutral monomers, such as alkenes or acrylates. Other synonyms for PVP include povidone, polyvidone, 1-vinyl-2-pyrrolidinone, and I-ethenyl-2-pyrolionone (CAS registry number 9003-39-8). The PVP used in the present invention suitably has a weight average molecular weight of about 10,000 to 250,000, preferably 30,000 to 100,000. Such materials are sold by various companies, including ISP Technologies, Inc. under the trademark PLASDONE™ K-29/32, from BASF under the trademark KOLLIDON™ for USP grade PVP, for example KOLLIDON™ K-30 or K-90. While the invention is not limited to any specific PVP, K-90 PVP is preferred, more preferably pharmaceutical grade.

The colored lens care solutions according to the invention are preferably formulated in such a way that they are isotonic with the lachrymal fluid. A solution which is isotonic with the lachrymal fluid is generally understood to be a solution whose concentration corresponds to the concentration of a 0.9% sodium chloride solution (308 mOsm/kg). Deviations from this concentration are possible throughout, provided that the contact lenses to be treated are not damaged.

The isotonicity with the lachrymal fluid, or even another desired tonicity, may be adjusted by adding organic or inorganic substances which affect the tonicity. Suitable ocularly acceptable tonicity agents include, but are not limited to sodium chloride, potassium chloride, glycerol, propylene glycol, polyols, dexpanthenol, mannitols, xylitol, sorbitol, and mixtures thereof. Preferably, the majority of the tonicity of the solution is provided by one or more compounds selected from the group consisting of non-halide containing electrolytes (e.g., sodium bicarbonate) and non-electrolytic compounds. The tonicity of the solution is typically adjusted to be in the range from about 200 to about 450 milliosmol (mOsm), preferably from about 250 to 350 mOsm.

In accordance with the invention the colored lens care solution can further comprise a surfactant for cleaning the contact lens. Any suitable known surfactants can be used in the invention. Examples of suitable surfactants include, but are not limited to poloxamers under the tradename Pluronic from BASF Corp. (Pluronic™ and Pluronic-R™) which are nonionic surfactants consisting of block copolymers of propylene oxide and ethylene oxide; poloxamine which is a block copolymer derivative of ethylene oxide and propylene oxide combined with ethylene diamine; tyloxapol, which is 4-(1,1,3,3-tetramethylbutyl)phenol polymer with formaldehyde and oxirane; ethoxylated alkyl phenols, such as various surface active agents available under the tradenames TRITON (Union Carbide, Tarrytown, N.Y., USA) and IGEPAL (Rhone-Poulenc, Cranbury, N.J., USA); polysorbates such as polysorbate 20, including the polysorbate surface active agents available under the tradename TWEEN (ICI Americas, Inc., Wilmington, Del., USA.); alkyl glucosides and polyglucosides such as products available under the tradename PLANTAREN (Henkel Corp., Hoboken, N.J., USA); and polyethoxylated castor oils commercially available from BASF under the trademark CREMAPHOR.

Preferred surfactants include homopolymers of polyethylene glycol or polyethyleneoxide, and certain poloxamers such as materials-commercially available from BASF under the tradenames PLURONIC® 17R4, PLURONIC® F-68NF, PLURONIC® F68LF, and PLURONIC® F127, with PLURONIC® F-68NF (National Formulary grade) being the most preferred. More preferably, a combination of PLURONIC® 17R4 and PLURONIC® F127 is used. When present, poloxamers may be employed at from about 0.001% to about 5% by weight, preferably from about 0.005% to about 1% by weight, more preferably from about 0.05% to about 0.6% by weight.

The colored lens care solutions according to the invention are produced in known manner, in particular by means of conventional mixing of the constituents with water or dissolving the constituents in water.

In accordance with the invention, a proteolytic enzyme is any protein capable of degrading a protein based on proteolysis. Proteases are such enzymes which degrade proteins. Examples of preferred proteases are subtilisin, trypsin, and papain, with subtilisin as the most preferred protease. Preferably, the proteolytic enzyme is immobilized on a solid support, such as, for example, glass or plastic beads, resins, or the like.

In accordance with the invention, the proteolytic enzyme can be added into a lens case where a contact lens will be disinfected with a colored lens care solution of the invention The proteolytic enzyme can be added in the lens case prior to or after filling the lens case with the colored lens care solution. The order is not important. The proteolytic enzyme can be in any forms, such as, for example, a table (e.g., Unizyme tablet from CIBA Vision).

There are some advantages associated with the invention. First, visual observation of color disappearance of a colored lens care solution gives customers a useful tool to monitor the disinfecting and cleaning of contact lenses by a colored lens care solution. Color is often used as a useful tool to codify information. By using the invention, a lens care solution's color changes from blue (initial color) to colorless, once contact lenses have been treated by the solution for a time period sufficient to disinfect and clean them. Such color disappearance can advantageously codify the length of time for disinfecting contact lenses. Second, the proteolytic enzyme only degrades selectively the colored protein in a colored lens care solution, since the colored protein is the only protein material. Other components in the lens care solution will not be degraded and as such one can easily preserve the antimicrobial and cleaning efficacies of a lens care solution. Thus, one can prepare a colored lens care solution of the invention directly by adding a colored protein into a commercially available lens care solution without significant changes in the properties of the original lens care solution. Third, the proteolytic enzyme can also play a role in cleaning contact lenses by removing proteinaceous materials from worn lenses, since tear fluids contain various proteins which can be adsorbed onto the surface of contact lenses or absorbed by the bulk lens material of contact lenses.

A lens case typically comprises a main body portion which includes a pair of separate and discrete wells (cavities or reservoirs) each adapted to receive one contact lens and an amount of a lens care solution. Each well has an open end having a substantially circular, oval or rain-drop shape periphery defining an opening. The lens case further comprises one or two caps adapted to be affixed to the wells at their open ends so as to provide a substantially liquid-impermeable seal. The caps each further include a sealing rim or surface adapted to mate with the peripheries surrounding wells. The lens case may be constructed of a material which is sturdy and impervious to chemicals contained in a lens solution. For example, polystyrene, high-density polyethylene, or polypropylene can be the construction material of choice, although others may be used.

Preferably, a protease immobilized on a solid support can be placed either in a well of a lens case for holding a contact lens and a given amount of a lens care solution or in a lens case's compartment in fluid communication with the well of the lens case In a preferred embodiment, a protease is placed into a pinwheel configuration within the confines of a lens case, as described in a co-pending patent application entitled "Len's Care Methods and Kits", herein incorporated by reference in its entirety. This pinwheel configuration is covered with a top that allows only a small piece of the pinwheel to be exposed to the lens care solution. After a number of uses (i.e., disinfection of a contact lens), the top of the pinwheel is rotated to allow a fresh amount of protease to be exposed to the lens care solution and as such, the colorant can be degraded by fresh protease.

The kit can optionally include instructions for how to use the lens care solution to clean and lubricate contact lenses directly in eyes.

The contact lens can be contacted with the solution by immersing the lens in a colored lens care solution of the invention in a lens case. Although not necessary, the solution containing the contact lens can be agitated, for example, by shaking the lens case containing the solution and contact lens, to at least facilitate removal of deposited material from the lens.

In another aspect, the invention provides a method for cleaning and/or disinfecting a contact lens. The method comprises the steps of: bringing one or more contact lenses into contact with a colored lens care solution in a lens case containing a proteolytic enzyme; and observing the change in the color of the colored lens care solution, substantially decolorization of the colored lens care solution indicating that the lenses being disinfected and cleaned by the colored lens care solution are ready for use.

The above described various embodiments can be used in this aspect of the invention.

The solutions and methods of the present invention may be used in conjunction with enzymes to remove debris or deposit material from the contact lens as the solutions of the present invention have no negative effect on the proteolytic activity of enzymes, such as UNIZYME®. After such contacting step, the contact lens optionally may be manually rubbed with saline, or even rinsed without rubbing, to remove further deposited material from the lens. The cleaning method can also include rinsing the lens substantially free of the liquid aqueous medium prior to returning the lens to a wearer's eye.

The previous disclosure will enable one having ordinary skill in the art to practice the invention. In order to better enable the reader to understand specific embodiments and the advantages thereof, reference to the following examples is suggested.

EXAMPLE 1

Blue protein. Several forms of the LinaBlue protein colorant are evaluated. A blue solution is obtained using raw powdered algae from Health and Herbs which is crushed with a mortar and pestle and centrifuged to pellet the cellular debris. LinaBlueAE and LinaBlueHGE are obtained from Dainippon, and purified allophycocyanin and phycocyanin are from Sigma. LinaBlue colorant is used in further studies because it has been used in the Blue Vision lens care product (CIBA Vision).

Lens soaking studies have been conducted with LinaBlueAE in Aquify® MPS. No color uptake is observed with LinaBlueAE for 21 days.

LinaBlue is used to prepare two colored lens care solutions as shown in Table 1.

TABLE 1

|  | Formulation I | Formulation II |
|---|---|---|
| PHMB | 1.05 ppm | 1 ppm |
| 50% Dexpanthenol | 21 g/l | 0.41 g/L |
| Pluronic F 127 | 1.0 g/l | 1.0 g/L |
| EDTA | 0.250 g/l | 0.04 g/L |
| Sorbitol | 18.8 g/l | 40.00 g/L |
| $NaH_2PO_4$ | 4.6 g/l | 3.00 g/L |
| Tris-Buffer (Tromethamine) | 3.32 g/l | 1.66 g/L |
| Tyloxapol |  | 0.20 g/L |
| Povidine |  | 2.00 g/L |
| LinaBlue | 97 mg/L | 97 mg/L |
| USP Purified Water | QS to batch size | |

Protease Selection. Three proteases are tested: subtilisin, trypsin, and papain. All three proteases can decolorize LinaBlueAE, as well as the other forms of the protein. Subtilisin is chosen because it has been approved for use in ophthalmic products, such as, Unizyme tablet (CIBA Vision). Subtilisin can be obtained from Novozyme as a product called Clear Lens Pro (CLP). A liquid sample of CLP directly from Novozyme is used for testing.

Decolorization Kinetics. Experiments are carried out to study the kinetics of decolorization of LinaBlue in the presence of Clear Lens Pro (CLP) and Unizyme tablets. The results demonstrate that a LinaBlueAE solution can be decolorized within the 4-6 hour time window.

In other experiments, CLP is nonspecifically bound (0.125 U/well) to a 6 well microtiter plate and then this plate is exposed to a lens care solution containing LinaBlueAE. Decolorization is achieved.

EXAMPLE 2

Subtilisin from Sigma is mobilized on various resins: Amberlite XAD7HP, and beads EC-HA and EC-EP (the difference being the functional groups on the surface, amine and epoxy, respectively). Subtilisin is deactivated after attachment to the Amberlite. Subtilisin is still active after immobilization onto the beads, and remains active up to 9 days post-attachment. There is some loss in activity from the non-immobilized enzyme. Subtilisin immobilized on the beads is able to be reused successfully up to 7 times, however some loss of activity is seen with subsequent decolorization reactions.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Furthermore, titles, headings, or the like are provided to enhance the reader's comprehension of this document, and should not be read as limiting the scope of the present invention. Accordingly, the spirit and scope of the appended claims should not be limited to the description of the preferred versions contained therein.

What is claimed is:

1. A lens care kit for cleaning and disinfecting contact lenses, comprising:
   a colored lens care solution including a water-soluble colored protein and a microbicide;
   and a proteolytic enzyme immobilized on a solid support, wherein the colored lens care solution is a multiple purpose solution and the colored lens care solution is free of hydrogen peroxide,
   wherein, when in contact with the colored lens care solution, the proteolytic enzyme degrades the colored protein over a time period sufficient to substantially decolorize the colored lens care solution, thereby indicating that lenses being disinfected and cleaned by the colored lens care solution are ready for use.

2. The lens care kit of claim 1, wherein the proteolytic enzyme is subtilisin, trypsin, papain, or combination thereof.

3. The lens care kit of claim 1, wherein the kit comprises a lens case having a well for holding a contact lens to be treated and an amount of the colored lens care solution, a compartment in fluid communication with the well, wherein the proteolytic enzyme on a solid support is placed in the compartment of the lens case.

4. The lens care kit of claim 3, wherein the colored protein is phycobiliprotein, phycocyanine, allophycocyanine, phycoerythrin, green fluorescent proteins (GFPs), GFP-like proteins, bacteriorhodopsin, or combination thereof.

5. The lens care kit of claim 3, wherein the colored protein is phycocyanine, allophycocyanine, or combination thereof.

6. The lens care kit of claim 3, wherein the colored protein is an algal extract selected from the group consisting of LinaBlue AE, LinaBlue HGE, LinaBlue A, LinaBlue HK, Lineablue HG, and combination thereof.

7. The lens care kit of claim 3, wherein the colored protein is purified allophycocyanin, purified phycocyanin, or combination thereof.

8. The lens care kit of claim 1, wherein the microbicide is a hexamethylene biguanide polymer (PHMB).

9. The lens care kit of claim 8, wherein the PHMB is present in an amount of from about 0.01 to about 10 ppm.

10. The lens care kit of claim 9, wherein the colored lens care solution initially has a color of blue or green or purple.

11. The lens care kit of claim 10, wherein after the colored lens care solution is in contact with the proteolytic enzyme, the color of the colored solution gradually fades over a controlled time period.

12. The lens care kit of claim 11, wherein, at the end of the controlled time period, the color of the colored lens care solution is substantially decolorized and becomes substantially clear and colorless.

13. The lens care kit of claim 12, wherein the controlled time period is sufficiently long for disinfecting contact lenses.

14. The lens care kit of claim 13, wherein the controlled time period is at least about 2 hour.

15. The lens care kit of claim 13, wherein the controlled time period is at least about 4 hours.

16. The lens care kit of claim 13, wherein the controlled time period is at least about 6 hours.

* * * * *